(12) United States Patent
Adachi et al.

(10) Patent No.: US 11,542,307 B2
(45) Date of Patent: Jan. 3, 2023

(54) β-GLUCAN-BINDING PROTEIN, β-GLUCAN DETECTION KIT, ARTIFICIAL DNA, AND BACTERIUM

(71) Applicant: TOEI SHINYAKU CO., LTD., Tokyo (JP)

(72) Inventors: Yoshiyuki Adachi, Tokyo (JP); Naohito Ohno, Tokyo (JP); Masuro Motoi, Tokyo (JP); Akitomo Motoi, Tokyo (JP)

(73) Assignee: TOEI SHINYAKU CO., LTD., Tokyo (JP)

( * ) Notice: Subject to any disclaimer, the term of this patent is extended or adjusted under 35 U.S.C. 154(b) by 0 days.

(21) Appl. No.: 17/616,853

(22) PCT Filed: Jun. 2, 2020

(86) PCT No.: PCT/JP2020/021820
§ 371 (c)(1),
(2) Date: Dec. 6, 2021

(87) PCT Pub. No.: WO2020/246478
PCT Pub. Date: Dec. 10, 2020

(65) Prior Publication Data
US 2022/0213152 A1 Jul. 7, 2022

(30) Foreign Application Priority Data
Jun. 7, 2019 (JP) .............................. JP2019-107248

(51) Int. Cl.
*C07K 14/00* (2006.01)
*C07K 14/435* (2006.01)
*G01N 33/579* (2006.01)

(52) U.S. Cl.
CPC ..... *C07K 14/43509* (2013.01); *G01N 33/579* (2013.01); *G01N 2333/43504* (2013.01)

(58) Field of Classification Search
None
See application file for complete search history.

(56) References Cited

U.S. PATENT DOCUMENTS

2014/0356886 A1* 12/2014 Yoneda .............. G01N 33/5308
435/320.1

FOREIGN PATENT DOCUMENTS

JP 2008-273917 11/2008

OTHER PUBLICATIONS

International Search Report dated Jun. 30, 2020 in International (PCT) Application No. PCT/JP2020/021820.
Kanagawa, Mayumi et al., "Structural Insights into Recognition of Triple-helical beta-Glucans by an Insect Fungal Receptor", Journal of Biological Chemistry, 2011, vol. 286, pp. 29158-29165.
Adachi, Yoshiyuki et al., "N-Terminal (1-3)-beta-D-Glucan Recognition Proteins from Insects Recognize the Difference in Ultra-Structures of (1-3)-beta-D-Glucan", International Journal of Molecular Sciences, 2019, vol. 20, article 3498, 14 pages.
Yamanaka, Daisuke et al., "Development of a novel beta-1, 6-glucan-specific detection system using functionally-modified recombinant end-beta-1, 6-glucanase", J. Biol. Chem, 2020, vol. 295, pp. 5362-5376.

* cited by examiner

*Primary Examiner* — Michael D Pak
(74) *Attorney, Agent, or Firm* — Wenderoth, Lind & Ponack, L.L.P.

(57) ABSTRACT

The β-glucan-binding protein contains an amino acid sequence represented by SEQ ID NO: 1.

10 Claims, 14 Drawing Sheets

Specification includes a Sequence Listing.

FIG. 1

AMINO ACID AND DNA SEQUENCE OF ARTIFICIAL BGRP

```
  1 M  N  H  K  V  H  H  H  H  H  H  I  E  G  R  H  M  E  L  G  20
256 ATGAATCACAAAGTGCATCATCATCATCATCATATCGAAGGTAGGCATATGGAGCTCGGT 315
 21 T  Y  E  V  P  D  A  K  L  E  A  I  Y  P  K  G  L  R  V  S  40
316 ACCTATGAAGTGCCTGATGCGAAACTCGAAGCCATTTACCCCAAAGGGTTACGCGTTAGC 375
 41 I  P  D  D  G  F  S  L  F  A  F  H  G  K  L  N  E  E  M  E  60
376 ATTCCGGATGATGGCTTTTCGCTGTTTGCCTTCCATGGGAAACTGAACGAGGAGATGGAA 435
 61 G  L  E  A  G  T  W  S  R  D  I  T  K  A  K  N  G  R  W  T  80
436 GGTCTGGAAGCTGGAACTTGGAGTCGGGACATCACGAAAGCGAAGAACGGTCGTTGGACC 495
 81 F  R  D  R  N  A  E  L  K  I  G  D  K  I  Y  F  W  T  Y  V  100
496 TTTCGTGACCGCAATGCAGAGCTGAAAATTGGCGACAAGATCTACTTCTGGACCTACGTC 555
101 I  K  D  G  L  G  Y  R  Q  D  N  G  E  W  T  V  T  G  Y  V  120
556 ATCAAAGATGGCTTGGGTTATCGCCAGGATAACGGAGAATGGACCGTAACGGGCTATGTG 615
121 D  E  D  G  N  P  V  D  T  D  G  P  T  T  T  P  T  G  S  E  140
616 GACGAAGATGGCAATCCGGTTGATACCGATGGTCCGACTACGACACCAACCGGATCCGAA 675
141 F  K  L  V  D  L  Q  S  R  *  150
676 TTCAAGCTTGTCGACCTGCAGTCTAGATAG 705
```

FIG. 2

AMINO ACID AND DNA SEQUENCE OF BGRP DERIVED FROM SILKWORM
Bombyx mori

```
  1 M   N   H   K   V   H   H   H   H   H   H   I   E   G   R   H   M   E   L   G  20
256 ATGAATCACAAAGTGCATCATCATCATCATCATATCGAAGGTAGGCATATGGAGCTCGGT 315
 21 T   Y   E   A   P   P   A   T   L   E   A   I   H   P   K   G   L   R   V   S  40
316 ACCTACGAGGCACCACCGGCCACGCTCGAAGCAATACACCCTAAAGGACTTAGGGTTTCT 375
 41 V   P   D   E   G   F   S   L   F   A   F   H   G   K   L   N   E   E   M   E  60
376 GTTCCTGATGAGGGCTTCTCGTTATTCGCGTTTCACGGTAAGCTCAACGAGGAAATGGAA 435
 61 G   L   E   A   G   H   W   S   R   D   I   T   K   P   K   N   G   R   W   I  80
436 GGCTTAGAGGCCGGCCATTGGTCCAGGGACATCACGAAGCCAAAAAACGGAAGATGGATA 495
 81 F   R   D   R   N   A   A   L   K   I   G   D   K   I   Y   F   W   T   F   V 100
496 TTCAGAGATCGAAATGCTGCGCTGAAAATCGGAGATAAGATTTACTTTTGGACTTTTGTC 555
101 I   K   D   G   L   G   Y   R   Q   D   N   G   E   W   T   V   E   G   F   V 120
556 ATAAAGGACGGCTTAGGATACAGACAGGATAACGGGGAGTGGACAGTTGAAGGTTTCGTA 615
121 D   E   A   G   N   P   V   N   T   E   G   S   E   I   T   P   G   V   E   F 140
616 GATGAAGCCGGTAATCCAGTAAACACAGAGGGCTCTGAAATAACACCAGGAGTAGAATTC 675
141 G   S   E   F   K   L   V   D   L   Q   S   R   * 153
676 GGATCCGAATTCAAGCTTGTCGACCTGCAGTCTAGATAG 714
```

FIG. 3

```
SupBGRP  1   MNHKVHHHHHHIEGRHMELGTYEVPDAKLEAIYPKGLRVSIPDDGFSLFAFHGKLNEEME  60
             MNHKVHHHHHHIEGRHMELGTYE P A LEAI+PKGLRVS+PD+GFSLFAFHGKLNEEME
BmBGRP   1   MNHKVHHHHHHIEGRHMELGTYEAPPATLEAIHPKGLRVSVPDEGFSLFAFHGKLNEEME  60

Sup     61   GLEAGTWSRDITKAKNGRWTFRDRNAELKIGDKIYFWTYVIKDGLGYRQDNGEWTVTGYV  120
             GLEAG WSRDITK KNGRW FRDRNA LKIGDKIYFWT+VIKDGLGYRQDNGEWTV G+V
Bm      61   GLEAGHWSRDITKPKNGRWIFRDRNAALKIGDKIYFWTFVIKDGLGYRQDNGEWTVEGFV  120

Sup    121   DEDGNPVDTDGPTTTPT---GSEFKLVDLQSR*  150
             DE GNPV+T+G  TP    GSEFKLVDLQSR*
Bm     121   DEAGNPVNTEGSEITPGVEFGSEFKLVDLQSR*  153
```

A: SupBGRP, B: BmBGRP, C: TcBGRP. Concentration of SPG and AT-SPG was 0-1000 ng/mL.

FIG. 10

| pH(± 0.1) | Solution1 | | Solution2 | | Adjust | Total |
|---|---|---|---|---|---|---|
| 0 | 1M HCl | | | | | |
| 1 | 0.1M HCl | | | | | |
| 2 | 0.2M KCl | 5mL | | | 5N HCl | 20mL |
| 3 | 0.1M Citric acid | 7.92mL | 0.2M Na₂HPO₄ | 2.1mL | | 20mL |
| 4 | 0.1M Citric acid | 6.14mL | 0.2M Na₂HPO₄ | 3.86mL | | 20mL |
| 5 | 0.1M Citric acid | 4.86mL | 0.2M Na₂HPO₄ | 5.14mL | | 20mL |
| 6 | 0.2M NaH₂PO₄ | 8.67mL | 0.2M Na₂HPO₄ | 1.33mL | | 20mL |
| 7 | 0.2M NaH₂PO₄ | 3.9mL | 0.2M Na₂HPO₄ | 6.1mL | | 20mL |
| 8 | 0.2M NaH₂PO₄ | 0.53mL | 0.2M Na₂HPO₄ | 9.47mL | | 20mL |
| 9 | 0.1M Tris | 10mL | | | 5N HCl | 20mL |
| 9.5 | 0.1M Glycine | 10mL | | | 5N NaOH | 20mL |
| 10 | 0.1M Glycine | 10mL | | | 5N NaOH | 20mL |
| 10.5 | 0.1M Glycine | 10mL | | | 5N NaOH | 20mL |
| 11 | Na₂HPO₄·12H₂O | 0.693g | Na₃PO₄·12H₂O | 0.014g | 5N NaOH | 20mL |
| 11.5 | Na₂HPO₄·12H₂O | 0.634g | Na₃PO₄·12H₂O | 0.041g | 5N NaOH | 20mL |
| 12 | Na₂HPO₄·12H₂O | 0.500g | Na₃PO₄·12H₂O | 0.102g | 5N NaOH | 20mL |
| 13 | 0.1M NaOH | | | | | |
| 14 | 1M NaOH | | | | | |

β-GLUCAN-BINDING PROTEIN, β-GLUCAN DETECTION KIT, ARTIFICIAL DNA, AND BACTERIUM

TECHNICAL FIELD

The present invention relates to a β-glucan-binding protein, a β-glucan detection kit, an artificial DNA, and a bacterium.

BACKGROUND ART

A β-glucan is a major constituent polysaccharide that constitutes a fungal cell wall, and as the β-glucan, β-1,3-glucan that is a polysaccharide consisting of β-(1→3)-linked glucose, β-1,6-glucan composed of β-(1→6)-linked glucose, and the like are known.

Further, for example, deep mycosis is an infectious disease that can be fatal due to the delayed initiation of the treatment, and for the early diagnosis toward the selection of an appropriate antimicrobial agent, fungal detection using β-glucan as a molecular marker has been performed.

Specifically, for example, Limulus factor G that is a β-1,3-glucan recognition protein derived from a horseshoe crab is used as an in-vitro diagnostic drug for detecting β-1,3-glucan in human blood. Further, a β-glucan-binding protein derived from a factor-G α subunit of a horseshoe crab blood cell component, and as the method for measuring β-glucan using the β-glucan-binding protein, a technique of Patent Literature 1, are known.

Furthermore, β-glucan has been attracting attention as an immunomodulatory natural product from long ago, and in recent years, the development of functional foodstuff containing β-glucan has been expected, and thus it has been desired to establish a technique for detecting and measuring β-glucan also in such a field.

In addition, as the β-glucan-binding protein, native proteins derived from various kinds of insects are known, and the amino acid sequences of the native proteins have been clarified (Non Patent Literature 1), but for example, depending on the conditions such as pH, and NaCl concentration, the binding stability may decrease, and the practicality for various uses has not been sufficient.

In view of the above circumstances, the group of the present inventors has created a new artificial β-glucan-binding protein that binds to β-glucan through intensive studies, and has reported on the binding stability and the like (Non Patent Literatures 2, and 3).

CITATION LIST

Patent Literature

Patent Literature 1: Re-publication of PCT International Publication No. 2010/107068

Non Patent Literature

Non Patent Literature 1: M. Kanagawa, T. Satoh, A. Ikeda, Y. Adachi, N. Ohno, Y. Yamaguchi, Structural insights into recognition of triple-helical beta-glucans by an insect fungal receptor, J. Biol. Chem., 286 (2011), 29158-29165
Non Patent Literature 2: P-054 Poster, The 60th Annual Meeting of the Japanese Society for Medical Mycology
Non Patent Literature 3: Abstract of 137th Annual Meeting of the Pharmaceutical Society of Japan

SUMMARY OF INVENTION

Technical Problem

However, in Non Patent Literatures 2 and 3, the characteristics of an artificial β-glucan-binding protein have been investigated, but the amino acid sequence and the like of a specific artificial β-glucan-binding protein have not been clarified at all so far.

The present invention has been made in view of the above-mentioned circumstances, and an object of the present invention is to provide a β-glucan-binding protein excellent in the stability of binding to β-glucan, a β-glucan detection kit, an artificial DNA, and a bacterium.

Solution to Problem

In order to solve the problems described above, the β-glucan-binding protein according to the present invention is characterized by containing an amino acid sequence represented by SEQ ID NO: 1.

The β-glucan detection kit according to the present invention is characterized by containing the β-glucan-binding protein described above.

The artificial DNA according to the present invention is characterized by encoding the β-glucan-binding protein described above.

The bacterium according to the present invention is characterized in that the artificial DNA described above is introduced into a bacterium.

Advantageous Effects of Invention

The β-glucan-binding protein (Sup BGRP) according to the present invention has higher β-glucan binding activity as compared with the Bm BGRP, Tc BGRP or the like in the natural form, and further is excellent in the stability against pH and heat.

According to the β-glucan detection kit of the present invention, it is hardly affected by pH and temperature, and β-glucan can be stably detected and quantified.

By introducing the artificial DNA according to the present invention into, for example, E. coli, a transformant that produces the β-glucan-binding protein (Sup BGRP) according to the present invention in a high yield can be obtained.

According to the bacterium of the present invention, the β-glucan-binding protein (Sup BGRP) according to the present invention can be obtained in a higher yield as compared with the Bm BGRP, Tc BGRP or the like in the natural form.

BRIEF DESCRIPTION OF DRAWINGS

FIG. 1 is a diagram showing the amino acid and DNA sequence of the β-glucan-binding protein (artificial BGRP: Sup BGRP) according to the present invention.

FIG. 2 is a diagram showing the amino acid and DNA sequence of BGRP derived from silkworm Bombyx mori.

FIG. 3 is a diagram showing the comparison of the amino acid sequences of Sup BGRP with Bm BGRP. In the amino acid sequence of the Sup BGRP, the amino acid residues that are different from those of the Bm BGRP are underlined.

FIG. 10 is a diagram showing the buffer solutions used in the investigation into the pH reactivity of BGRP.

DESCRIPTION OF EMBODIMENTS

Figure 4:
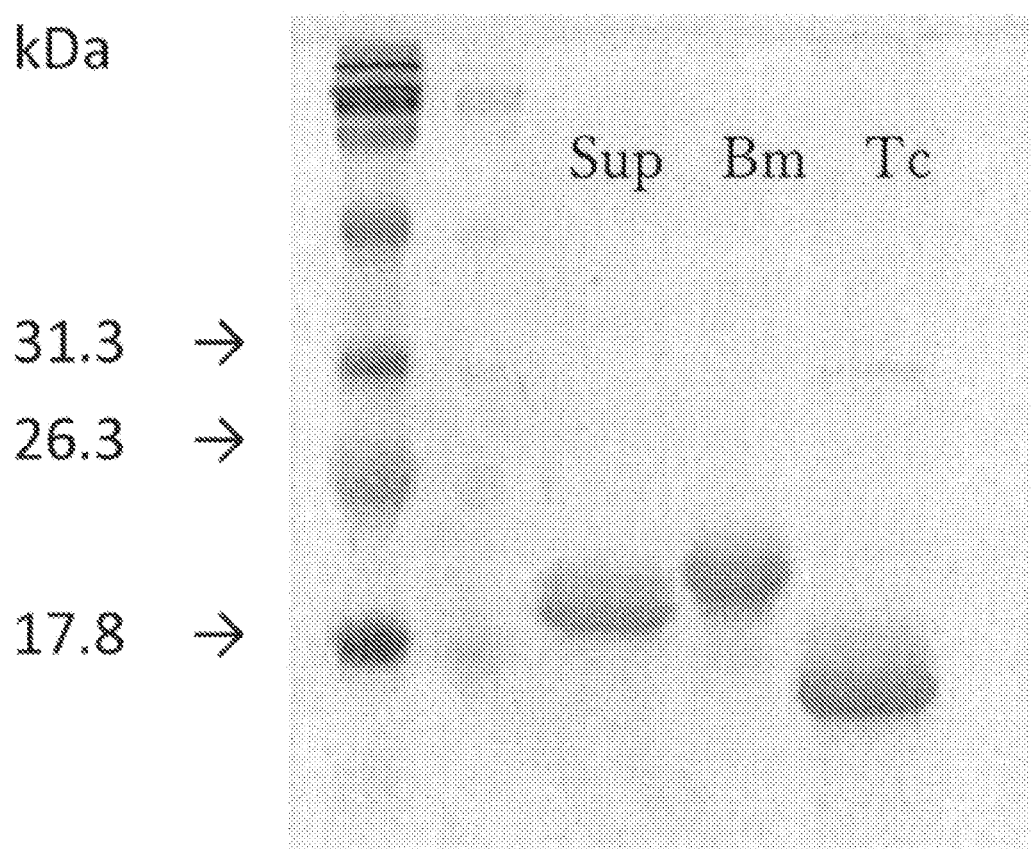
FIG. 4 is a diagram showing the results of SDS-PAGE of BGRPs (Sup BGRP, Bm BGRP and Tc BGRP).

Hereinafter, one embodiment of each of the β-glucan-binding protein, β-glucan detection kit, artificial DNA, and bacterium according to the present invention will be described.

β-Glucan-Binding Protein

The β-glucan-binding protein (Sup BGRP) according to the present invention contains the following amino acid sequence represented by SEQ ID NO: 1. This amino acid sequence is a β-glucan-binding protein (Sup BGRP) artificially prepared by introducing an amino acid mutation of around 36 residues (23 residues for silkworm) on the basis of the conventionally-known amino acid sequences of β-glucan-binding proteins (BGRPs) derived from various kinds of insects, for example, a silkworm and the findings so far of the present inventors.

```
                                        (SEQ ID NO: 1)
Met Asn His Lys Val His His His His His Ile

Glu Gly Arg His Met Glu Leu Gly Thr Tyr Glu Val

Pro Asp Ala Lys Leu Glu Ala Ile Tyr Pro Lys Gly

Leu Arg Val Ser Ile Pro Asp Asp Gly Phe Ser Leu

Phe Ala Phe His Gly Lys Leu Asn Glu Glu Met Glu

Gly Leu Glu Ala Gly Thr Trp Ser Arg Asp Ile Thr

Lys Ala Lys Asn Gly Arg Trp Thr Phe Arg Asp Arg
```

-continued
```
Asn Ala Glu Leu Lys Ile Gly Asp Lys Ile Tyr Phe

Trp Thr Tyr Val Ile Lys Asp Gly Leu Gly Tyr Arg

Gln Asp Asn Gly Glu Trp Thr Val Thr Gly Tyr Val

Asp Glu Asp Gly Asn Pro Val Asp Thr Asp Gly Pro

Thr Thr Thr Pro Thr Gly Ser Glu Phe Lys Leu Val

Asp Leu Gln Ser Arg
```

Although the β-glucan-binding protein (Sup BGRP) according to the present invention can be obtained by a known chemical or genetic engineering technique, a method for obtaining the β-glucan-binding protein (Sup BGRP) by being expressed with recombinant *E. coli* into which artificial DNA encoding the β-glucan-binding protein (Sup BGRP) according to the present invention has been introduced can be preferably mentioned. By expressing the β-glucan-binding protein (Sup BGRP) according to the present invention by *E. coli*, the β-glucan-binding protein (Sup BGRP) according to the present invention can be obtained in a higher yield as compared with the BGRP in the natural form derived from an insect.

Further, the β-glucan-binding protein (Sup BGRP) according to the present invention particularly has a strong binding ability to β-1,3 glucan or β-1,3-1,6 glucan. Examples of the β-glucan to which the β-glucan-binding protein (Sup BGRP) according to the present invention binds include Paramylon, Curdlan, Pachyman, Paramylon, CSBG (Candida-solubilized β-glucan), APBG (Aureobasidium β-glucan), SPG, Laminarin, Barley BG (barley β-glucan), and yeast β-glucan.

In addition, it is known that the triple helical structure of β-glucan dissociates the hydrogen bond by alkali and has partially a single helical structure, but the β-glucan-binding protein (Sup BGRP) according to the present invention has a strong binding ability to the β-glucan having a triple helical structure.

The β-glucan-binding protein (Sup BGRP) according to the present invention has higher β-glucan binding activity as compared with the Bm BGRP, Tc BGRP or the like in the natural form, and further is excellent in the stability against pH and heat.

As described above, the β-glucan-binding protein (Sup BGRP) according to the present invention is useful, for example, as a protein probe for the purpose of detecting and quantifying β-glucan, from the viewpoints of the ease of expression in *E. coli*, the yield, the stability against pH and heat in β-glucan-binding, and the like.

Further, into an amino acid sequence represented by SEQ ID NO: 1, for example, a peptide linker of hydrophilic amino acid of 10 to 30 residues can be inserted at an arbitrary position in order to enhance the efficiency of modification to a labeled product or a carrier.

β-Glucan Detection Kit

The β-glucan detection kit according to the present invention contains the above-described β-glucan-binding protein (Sup BGRP) according to the present invention, and further can also contain various kinds of materials for detecting and measuring β-glucan.

Specifically, the detection and measurement of β-glucan by using the β-glucan detection kit according to the present invention can be performed by bringing the β-glucan-binding protein (Sup BGRP) according to the present invention into contact with a test sample, forming a complex of the β-glucan-binding protein and the β-glucan in the test sample, and detecting the presence of this complex or quantifying the amount of the complex. Such detection and measurement can be performed in accordance with, for example, a direct adsorption method, a sandwich method, a competition method or the like in enzyme-linked immunosorbent assay (ELISA) method as the conventionally-known method (for example, Patent Literature 1 or the like). Further, by preparing a chromatography in which the β-glucan-binding protein (Sup BGRP) according to the present invention is immobilized on a carrier, the β-glucan in a solution sample can be separated and purified.

Accordingly, the β-glucan detection kit according to the present invention can contain various kinds of markers (labeling substances), carriers, and the like in accordance with these detection and measurement methods.

In one embodiment of the β-glucan detection kit according to the present invention, as the carrier, a material made of plastic, glass, gel, celluloid, paper, magnetic resin, polyvinylidene fluoride, nylon, nitrocellulose, agarose, latex, or polystyrene can be mentioned. Specifically, a carrier can contain an ELISA plate, a dipstick, a microtiter plate, a radioimmunoassay plate, beads, agarose beads, plastic beads, latex beads, magnetic beads, an immunoblotting membrane, or immunoblotting paper.

In one embodiment of the β-glucan detection kit according to the present invention, as the marker, a radiolabel, a fluorescent label, a chemiluminescent label, a chromophore label, a ligand, a fluorescein, a radioactive isotope, a phosphatase, a luciferase, biotin, biotin-related, avidin, an avidin-related compound, or the like can be mentioned.

Artificial DNA

The artificial DNA according to the present invention encodes the above-described β-glucan-binding protein (Sup BGRP) according to the present invention. Specifically, as the artificial DNA according to the present invention, an artificial DNA containing the following nucleotide sequence represented by SEQ ID NO: 2 can be mentioned. This artificial DNA can be prepared by using, for example, a known DNA automatic synthesizer or the like.

(SEQ ID NO: 2)
atgaatcacaaagtgcatcatcatcatcatcatatcgaaggtaggcatat ggagctcggtacctatgaagtgcctgatgcgaaactcgaagccatttacc ccaaagggttacgcgttagcattccggatgatggcttttcgctgtttgcc ttccatgggaaactgaacgaggagatggaaggtctggaagctggaacttg gagtcgggacatcacgaaagcgaagaacggtcgttggacctttcgtgacc gcaatgcagagctgaaaattggcgacaagatctacttctggacctacgtc atcaaagatggcttgggttatcgccaggataacggagaatggaccgtaac gggctatgtggacgaagatggcaatccggttgataccgatggtccgacta cgacaccaaccggatccgaattcaagcttgtcgacctgcagtctagatag Bacterium The bacterium according to the present invention is transformed by introducing the above-described artificial DNA according to the present invention into a bacterium. As the kind of the bacterium, for example, *E. coli, P seudomonas, Bacillus subtilis, Bacillus stearothermophilus*, yeast, other fungi, or the like can be mentioned, and *E. coli* is preferable.

For example, the artificial DNA according to the present invention is introduced into a bacterium such as *E. coli* by a plasmid vector or the like and transformed, and thus a bacterium expressing the β-glucan-binding protein (Sup BGRP) according to the present invention can be obtained. By expressing a protein by the bacterium according to the present invention, the β-glucan-binding protein (Sup BGRP) according to the present invention can be obtained in a higher yield as compared with the BGRP in the natural form derived from an insect.

The β-glucan-binding protein, β-glucan detection kit, artificial DNA, and bacterium according to the present invention are not limited to the above-described embodiments, and can be appropriately designed.

EXAMPLES

Hereinafter, the β-glucan-binding protein according to the present invention and the like will be described in detail by way of Examples, but the present invention is not limited to the following Examples at all.

As described above, the β-glucan-binding protein according to the present invention has an amino acid sequence represented by SEQ ID NO: 1 (FIG. 1). Hereinafter, the β-glucan-binding protein consisting of an amino acid sequence represented by SEQ ID NO: 1 may be described as "Sup BGRP" or "Sup".

Further, as the β-glucan-binding protein in the natural form, a protein derived from silkworm *Bombyx mori* may be described as "Bm BGRP" or "Bm" (FIG. 2). Furthermore, as the β-glucan-binding protein in the natural form, a protein derived from *Tribolium castaneum* may be described as "Tc BGRP" or "Tc"

Example 1 SDS-PAGE

A 2×SDS-Sample Buffer was mixed with each of the BGRP samples (Sup BGRP, Bm BGRP, and Tc BGRP) purified by His-Tag affinity chromatography so as to have a ratio of 1:1, and the obtained solution was vortexed and then boiled for 3 minutes to prepare a sample. A sample reagent was separated by using a Laemmli method at a 15% acrylamide gel concentration. As the molecular weight marker, DynaMarker Protein MultiColor Stable (BioDynamics Laboratory Inc.) was used.

Rapid CBB KANTO (KANTO CHEMICAL CO., INC.) was used for staining, and the staining was performed in accordance with the protocol.

As shown in FIG. 4, Sup BGRP, Bm BGRP, and Tc BGRP each showed a molecular weight of around from 17 to 18 kDa, and were all confirmed to be a single molecule.

Example 2 Expression of BGRP by *E. coli*

The gene transfer of each of the plasmids prepared on the basis of the DNA sequence (SEQ ID NO: 2) encoding Sup BGRP, and known DNA sequences encoding Bm BGRP and Tc BGRP was performed into an *E. coli* BL21 strain by using a heat shock method.

After that, ampicillin was added into Luria-Bertani (LB) medium so as to have a concentration of 0.01%, and 10 mL of the obtained medium was subjected to shaking culture at 37° C. overnight. The medium after the culture was filled up to 200 mL, and the medium was subjected to shaking culture at 37° C. up to the range of 0.4 to 0.6 of OD630. After the culture, the obtained medium was subjected to shaking culture at 15° C. for 30 minutes, and then IPTG was added in the medium so as to have a concentration of 100 μg/mL, and the resultant medium was subjected to shaking culture at 15° C. for 24 hours.

After the culture, the medium was centrifuged at 5000 rpm for 10 minutes, and the precipitation was suspended in TALON buffer, the cell wall was crushed with ultrasonic waves, and a protein was recovered. The protein was recovered in accordance with the protocol of TALON Metal Affinity Resin (TaKaRa) as the recovery method. After the recovery, the recovered protein was dialyzed with PBS, Proclin was added after the dialysis so as to have a concentration of 0.04%, and the obtained PBS solution was refrigerated and stored.

The yields of BGRPs (Sup BGRP, Bm BGRP, and Tc BGRP) by *E. coli* are shown in Table 1.

TABLE 1

|  | Protein conc. (mg/mL) | Volume (mL) | Total yield of BGRP (mg) |
|---|---|---|---|
| Sup | 2.0 | 1.5 | 3.0 |
| Bm | 0.8 | 1.5 | 1.2 |
| Tc | 1.7 | 1.5 | 2.5 |

As shown in Table 1, it has been confirmed that the recombinant Sup BGRP prepared by *E. coli* achieves a higher yield as compared with the BGRPs (Bm, and Tc) in the natural form.

Example 3 BGRP Binding Reactivity Test

<1> In the BGRP binding reactivity test, the β-glucans shown in the following Table 2 were used.

TABLE 2

| Polysaccharides | Structure | M.W. | Origin | Solvent |
|---|---|---|---|---|
| Barley glucan | β-1, 3-1, 4 |  | Barley | Water |
| Paramylon | β-1, 3 |  | *Euglena gracilis* | 1.0 M NaOH |
| Curdian | β-1, 3 |  | *Alcaligenes faecalis* | 1.0 M NaOH |
| Pachyman | β-1, 3-1, 6 | 42 kDa | *Poria cocos* | 0.5 M NaOH |
| CSBG | β-1, 3-1, 6 | Unknown | *Candida albicans* | DMSO |
| APBG | β-1, 3-1, 6 | 333-614 kDa | *Aureobasidium pullulans* | Water |
| SPG | β-1, 3-1, 6 | 450 kDa (900mer) | *Schizophyllum commune* | Saline |
| Laminarin | β-1, 3-1, 6 | 3'6 kDa (20mer) | *Laminarina digitata* | Water |

<2> First, the amount of immobilized BGRP in sandwich ELISA and the reactivity of β-glucan were investigated by using Candida BG (CSBG). Specifically, the amount of immobilized BGRP was investigated by the following technique.

(1) Preparation of Biotinylated BGRP

BGRP was dialyzed against 10 mM Bicine buffer (pH 8.0), and after the recovery, Biotin-(AC$_5$)$_2$-Sulfo-OSu (DOJINDO) was added into a protein solution. After mixing well, the solution was incubated at room temperature for 2 hours. After that, the incubated solution was dialyzed with PBS, Proclin was added after the dialysis so as to have a concentration of 0.04%, and the obtained solution was refrigerated and stored.

(2) Evaluation of Biotinylation Efficiency 3.5 mg of HABA was weighed out, and dissolved in 125 μL of dimethyl sulfoxide (DMSO) (HABA-DMSO solution). 2.5 mg of avidin was weighed out, and dissolved in PBS. Into the obtained PBS solution, 50 μL of the HABA-DMSO solution was added, and the resultant solution was filled up to 5 mL (HABA-Avidin solution). (+) Biotin was used as the standard and mixed with the HABA-Avidin solution, and the obtained solution was placed in a 384-well plate at 50 μL/well. A sample was also mixed with the HABA-Avidin solution, and the obtained solution was placed at 50 μL/well, similarly as in the standard. After that, the absorbance was measured at a measurement wavelength of 500 nm. The biotin concentration in the sample solution was calculated by using the calibration curve software attached. The protein concentration in the same sample solution was determined by a BCA method, and the molecular ratio (B/P ratio) of biotin:protein was calculated.

(3) Investigation of Amount of Immobilized BGRP Using Sandwich ELISA

Each BGRP was diluted with a 0.1 M phosphate buffer (pH 6.8) to concentrations of 20, 5, 1.25, 0.31, 0.08, and 0 μg/mL, and the diluted BGRP was placed in a 96-well NUNC ELISA plate at 50 μL/well and left to stand at 37° C. for 2 hours or at 4° C. overnight. After that, the plate was washed with PBST three times, and was left to stand at room temperature for 1 hour with BPBS. CSBG was diluted with BPBS to 100 ng/mL, and the diluted CSBG was placed in a plate at 50 μL/well, and the culture was performed at 37° C. for 1 hour. After the plate was washed with PBST three times, each Bio-BGRP was diluted with BPBS to a concentration of 0.5 μg/mL, the diluted Bio-BGRP was added in the plate at 50 μL/well, and the culture was performed at 37° C. for 1 hour. After the plate was washed with PBST three times, Streptavidin-HRP (BioLegend) was diluted with BPBS to a concentration of 0.2 μg/mL, the diluted Streptavidin-HRP was placed in the plate at 50 μL/well, and the culture was performed at 37° C. for 1 hour. After the plate was washed with PBST five times, TMB was placed in the plate at 50 μL/well, a stop solution was placed at 50 μL/well to terminate the reaction, and the measurement was performed with an absorbance at a measurement wavelength of 450 nm and a reference wavelength of 630 nm.

Figure 5:
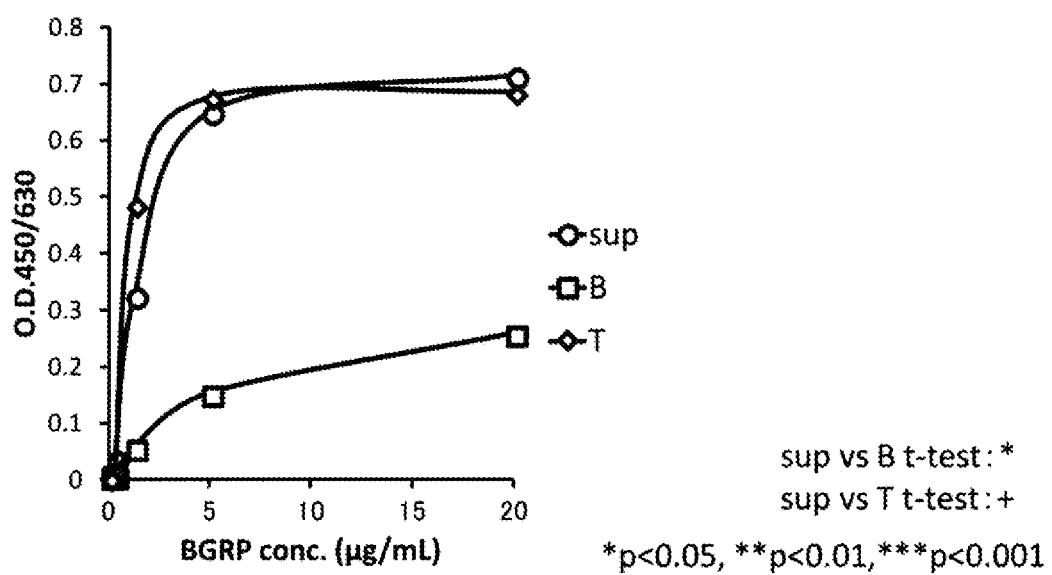
FIG. 5 is a diagram showing the results of the investigation into the reactivities of BGRPs (Sup BGRP, Bm BGRP, and Tc BGRP) and CSBG.

<3> Results are shown in FIG. 5. In the comparison of Bm BGRP with Sup BGRP, it has been confirmed that the Sup BGRP shows higher reactivity. In the comparison of Tc BGRP with Sup BGRP, it has been confirmed that both show almost the same reactivity as each other. In the three kinds of BGRPs, the decrease in the reactivity was observed when the BGRP concentration was 5 μg/mL or less, and thus, in the subsequent experiments, the concentration of immobilized protein was set to 5 μg/mL.

<4> Next, the reactive binding ability of BGRP in various kinds of β-glucans and other polysaccharides was investigated by a Sandwich ELISA method.

Each BGRP was diluted with a 0.1 M phosphate buffer (pH 6.8) to a concentration of 5 μg/mL, and the diluted BGRP was placed in a 96-well NUNC ELISA plate at 50 μL/well and left to stand at 37° C. for 2 hours or at 4° C. overnight. After that, the plate was washed with PBST three times, and was left to stand at room temperature for 1 hour with BPBS. Each β-glucan shown in Table 2 was diluted serially twice, the diluted β-glucan was placed in the plate, and the culture was performed at 37° C. for 1 hour. After the plate was washed with PBST three times, each Bio-BGRP was diluted with BPBS to a concentration of 0.5 μg/mL, the diluted Bio-BGRP was added in the plate at 50 μL/well, and the culture was performed at 37° C. for 1 hour. After the plate was washed with PBST, Streptavidin-HRP (BioLegend) was diluted with BPBS to a concentration of 0.2 μg/mL, the diluted Streptavidin-HRP was placed in the plate at 50 μL/well, and the culture was performed at 37° C. for 1 hour. After the plate was washed with PBST five times, TMB was placed in the plate at 50 μL/well, a stop solution was placed at 50 μL/well to terminate the reaction, and the measurement was performed with an absorbance at a measurement wavelength of 450 nm and a reference wavelength of 630 nm. Note that the ELISA in the following Examples was also performed in a similar way.

Figure 6:
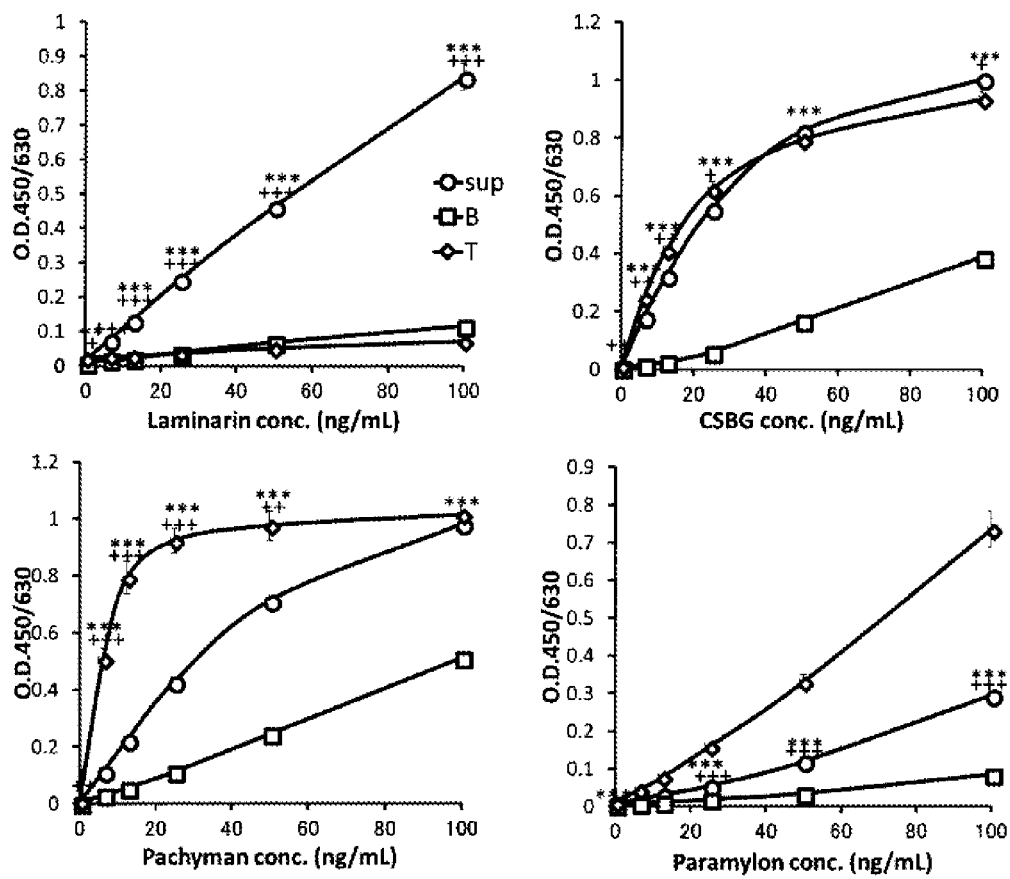
FIG. 6 is a diagram showing the results of the investigation into the reactivities of BGRPs (Sup BGRP, Bm BGRP, and Tc BGRP) and various kinds of β-glucans.
Figure 7:
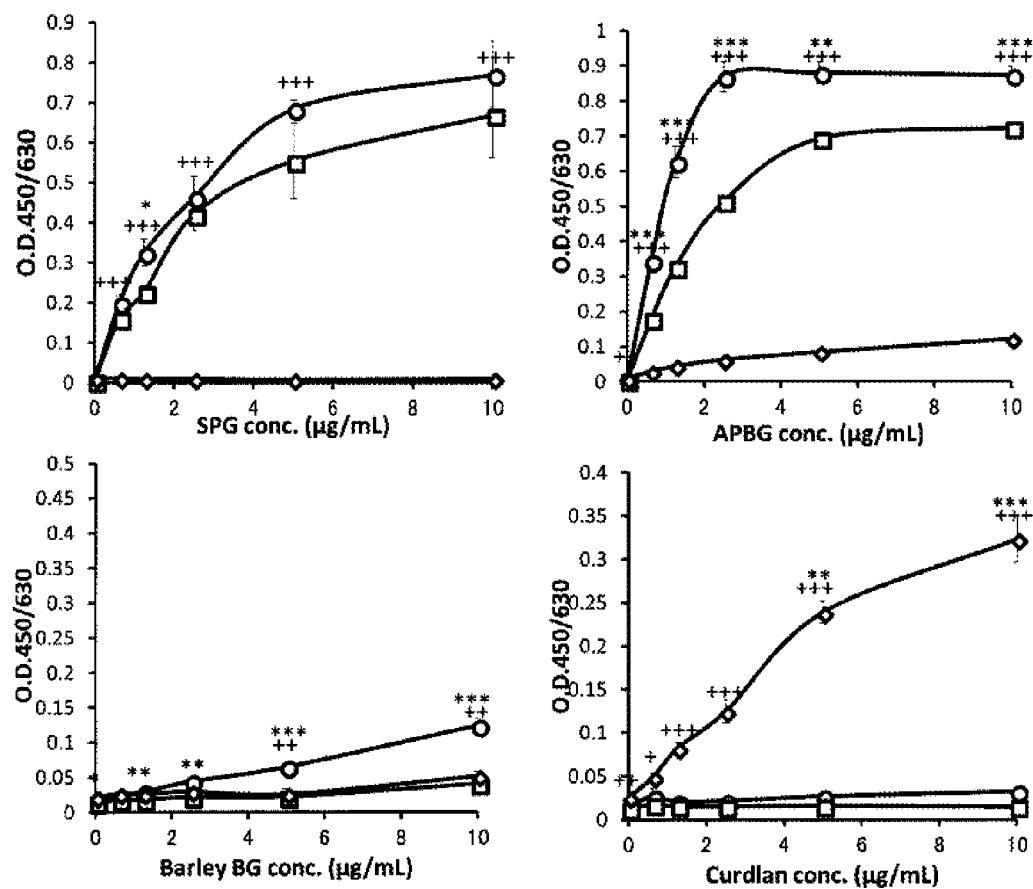
FIG. 7 is a diagram showing the results of the investigation into the reactivities of BGRPs (Sup BGRP, Bm BGRP, and Tc BGRP) and various kinds of β-glucans.

Results are shown in FIGS. 6 and 7.

In comparison of Sup BGRP with Bm BGRP, the Sup BGRP showed significantly higher binding ability as compared with the Bm BGRP in Candida BG (CSBG), Pachyman, and Paramylon. The Sup BGRP showed significantly higher binding ability as compared with the Bm BGRP in SPG, and black yeast BG (APBG). On the other hand, the reaction was hardly observed in the same concentration range as those of CSBG, Pachyman, and Paramylon (maximum concentration 100 ng/mL), and thus, it is considered that the reactivity is lower than those of these three kinds of BG.

In comparison of Sup BGRP with Tc BGRP, the Tc BGRP showed significantly higher binding ability as compared with the Sup BGRP in Candida BG (CSBG), Pachyman, and Paramylon. In the Paramylon, the binding ability of Tc BGRP was significant in all concentrations, while the significant binding ability of Tc BGRP was observed in intermediate concentrations in the Candida BG, and the Pachyman. It is considered that since Pachyman, Paramylon, and Curdlan are dissolved by using alkali, the higher-order structure of β-glucan is changed, and the binding ability of the Tc BGRP that easily binds to the β-glucan of the cleaved helical structure is high. The Sup BGRP showed significantly higher binding ability as compared with the Tc BGRP, in SPG, and black yeast BG (APBG). From this result, it is also considered that the Sup BGRP has binding specificity different from the Tc BGRP.

Further, Barley glucan hardly showed the binding ability in all of the BGRPs as compared with other β-glucans. The Barley glucan is known to have β-(1,3) binding and β-(1,4) binding, and it has been suggested that the reactivity of BGRP is reduced in the presence of the β-(1,4) binding.

Example 4 Investigation into Higher-Order Structure Specificity of β-Glucan in BGRP Binding Ability It is known that the triple helical structure of β-glucan dissociates the hydrogen bond by alkali and has partially a single helical structure. By using Laminarin and SPG, it was investigated in a similar manner as in Example 3 how the binding ability changed between the one retaining the triple helical structure and the one having a partially cleaved helical structure.

Figure 8:
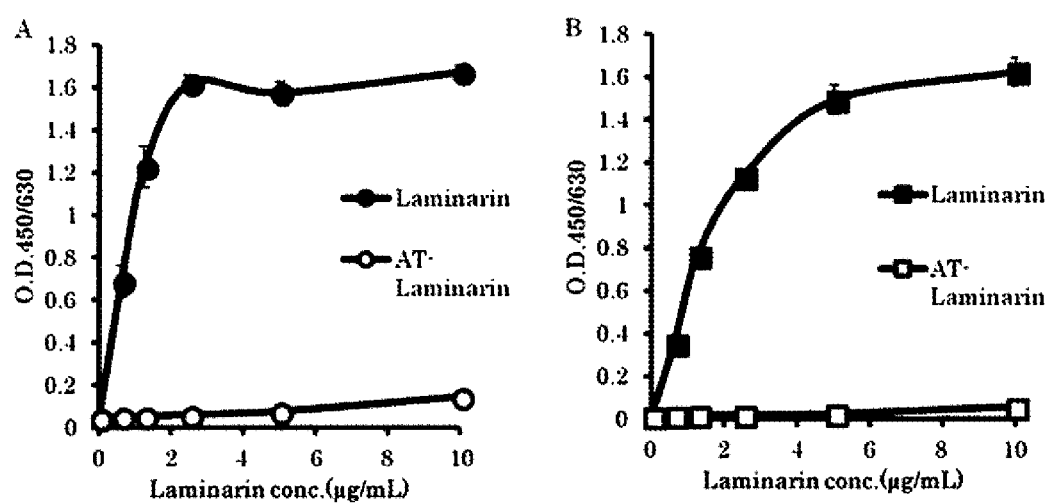
FIG. 8 is a diagram showing the results of the investigation into the higher-order structural specificity of β-glucan in the BGRP binding ability by using Laminarin. FIG. A shows Sup BGRP, and FIG. B shows Bm BGRP. The Laminarin and alkali-treated (AT)-Laminarin were set to 0 to 10 µg/mL.
Figure 9:
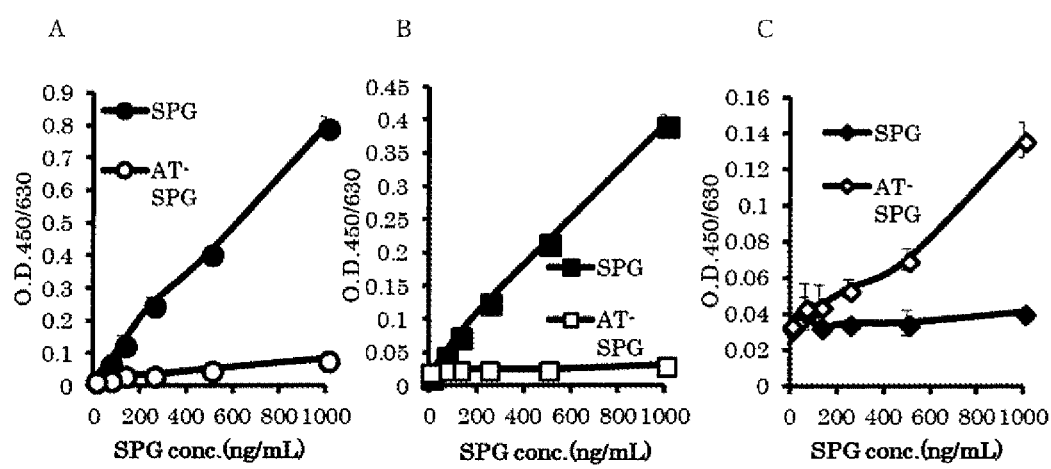
FIG. 9 is a diagram showing the results of the investigation into the higher-order structural specificity of β-glucan in the BGRP binding ability by using SPG. FIG. A shows Sup BGRP, FIG. B shows Bm BGRP, and FIG. C shows Tc BGRP. The SPG and alkali-treated (AT)-SPG were set to 0 to 1000 ng/mL.

Results are shown in FIGS. 8 and 9. Sup BGRP and Bm BGRP both showed relatively high reaction to alkali-untreated β-glucan, but the reaction decreased after performing alkali treatment. Tc BGRP hardly reacted with untreated β-glucan, but showed a reaction with alkali-treated β-glucan.

Accordingly, it has been suggested that Tc BGRP is easy to react with β-glucan having a single helical structure, and Sup BGRP reacts well with β-glucan having a triple helical structure.

Example 5 Investigation into pH Reactivity of BGRP

In order to examine the effect of BGRP on the binding ability due to the liquid property such as acid or alkali, investigation by ELISA was performed by using Britton-Robinson buffers (pH 3 to 12, BR-buffer) of universal buffer solution, buffer solutions (T2 buffer) shown in FIG. 10, and aqueous solutions obtained by changing only the NaCl concentration of PBS.

Figure 11:
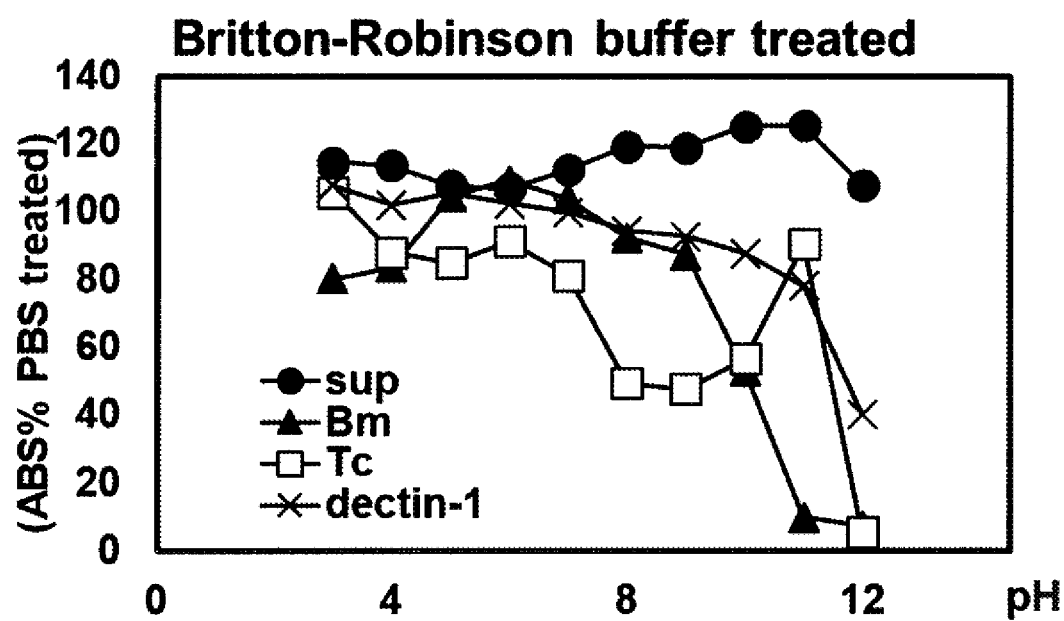
FIG. 11 is a diagram showing the results of the investigation into the pH reactivity of BGRP by using Britton-Robinson buffer (BR-buffer, pH 3 to 12).
Figure 12:
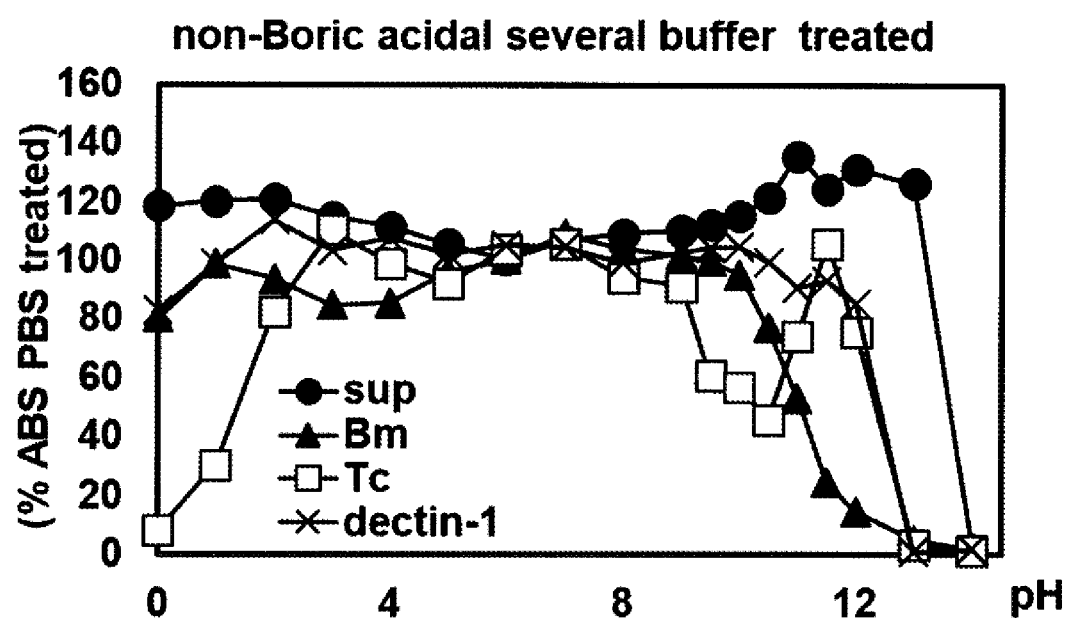
FIG. 12 is a diagram showing the results of the investigation into the pH reactivity of BGRP by using a buffer solution (T2 buffer) shown in FIG. 10 and aqueous solutions obtained by changing only the NaCl concentration of phosphate-buffered saline (PBS).

Results are shown in FIGS. 11 and 12. It has been confirmed that Sup BGRP retains the binding ability of β-glucan (Laminarin) in a wider pH range as compared with Bm BGRP, Tc BGRP, and dectin-1, and this property has the same tendency even if different kinds of buffer solutions are used.

Example 6 Investigation into Effect of NaCl Concentration on β-Glucan Binding Ability of BGRP In order to examine the effect of NaCl concentration on the binding ability of BGRP, the reactivity of BGRP with β-glucan (Laminarin) was investigated by ELISA with a reaction solution obtained by changing the NaCl concentration in a phosphate buffer solution.

Figure 13:
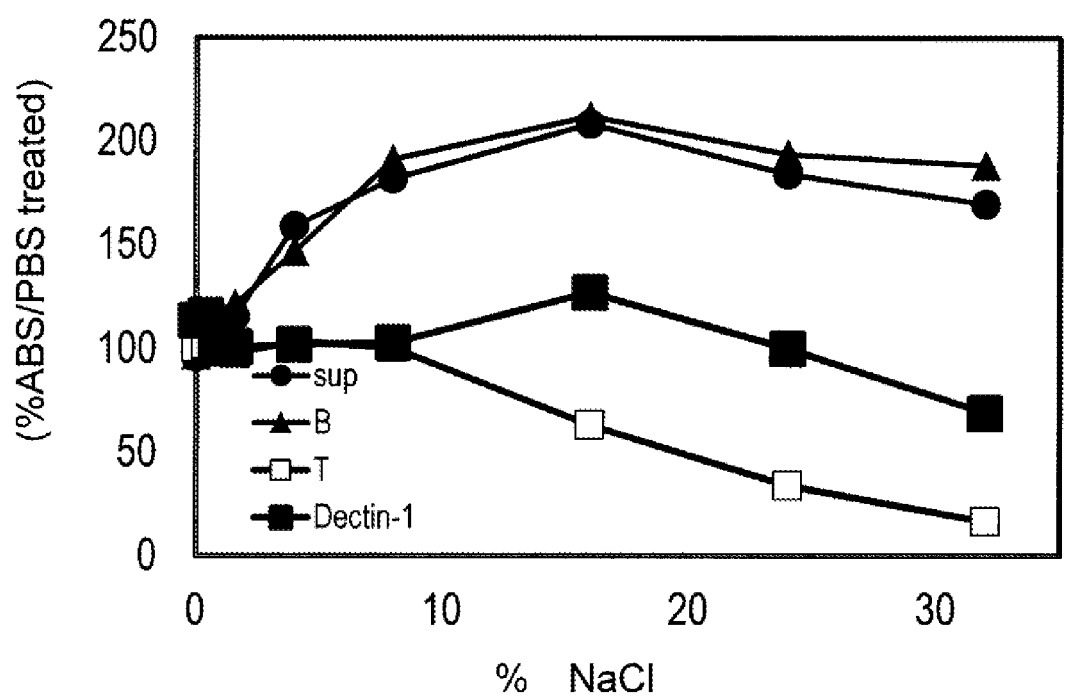
FIG. 13 is a diagram showing the results of the investigation into the effect of NaCl concentration on the β-glucan binding ability of BGRP.

Results are shown in FIG. 13. The β-glucan binding abilities of Tc BGRP and Dectin-1 were lowered with the increase in the NaCl concentration, but it has been confirmed that Sup BGRP and Bm BGRP show high β-glucan binding ability even in a high-salt concentration solution.

Example 7 Investigation into Changes in β-Glucan Binding Ability by Heat Treatment of BGRP <1> In order to investigate the heat stability of BGRP, PBS solutions of BGRPs (Sup BGRP, Bm BGRP, Tc BGRP, and Dectin-1) were treated at 40° C., 50° C., 60° C., 70° C., 80° C., and 90° C. for 30 minutes or treated in a freezer at −20° C. for 30 minutes, by using a thermal cycler.

The BGRP after the treatment at each temperature was compared by SDS-PAGE and Blue native PAGE (BN-PAGE)8).

For β-glucan, the changes in the binding ability were compared from the difference in the mobility on electrophoresis between a complex and a monomer by using Laminarin or CSBG (BGRP:BG=1:3).

Specifically, the SDS-PAGE was performed in a similar manner as in Example 1, and the BN-PAGE was performed by the following materials and methods.

Stock Solution

A solution: 1 M tricine/NaOH (pH 7.0), 1.79 g of tricine was dissolved in 5 mL of DIW and the pH was adjusted to 7.0 with 5 M NaOH. In the end, the pH-adjusted solution was diluted with DIW to prepare 10 ml of solution.

B solution: 1 M Bis-Tris/HCl (pH 7.0), 10.46 g of Bis-Tris was solubilized with 40 mL of DIW. The pH was adjusted to 7.0 with 6 M HCl, and then the pH-adjusted solution was diluted with DIW to prepare 50 mL of solution.

Acrylamide solution (48% acrylamide 1.5% bis-acrylamide aqueous solution): 19.2 g of acrylamide and 600 mg of bis-acrylamide were dissolved in 40 mL of DIW. 5×Sample buffer solution: 50 mg of CBB G-250 (TCI) and 6.5 mg of 6-amino-n-caproic acid (Wako) were weighed in a tube. Next, 100 μL of B solution was added. After that, into the obtained solution, a solution in which 17.4 μg of PMSF (Sigma) had been dissolved in EtOH was added. After that, the resultant solution was dissolved in DIW to be 1 mL in total. In the end, this buffer solution was mixed with glycerol at 1:1.

Buffer Solution

Buffer cathode buffer solution: 20 mg of CBB G-250 was weighed in a glass bottle, and 5 mL of A solution, 1.5 mL of B solution, and 93.5 mL of DIW were added into the glass bottle.

Anode buffer solution: 25 mL of B solution was diluted with DIW to 500 mL.

Gel buffer solution: 1.97 g of 6-amino-n-caproic acid was weighed in a tube. Next, 1.5 mL of B solution was poured into the tube. In the end, the obtained solution was diluted with DIW to 15 mL. The prepared solutions were all stored at 4° C. Gel preparation and electrophoresis were performed by using SE260 Mighty Small II Deluxe Mini Vertical Electrophoresis Unit (Hoefer).

Gel

Gel 10% separation gel: 4 mL of gel buffer, 1.6 mL of acrylamide solution, 1 mL of glycerol, 1.4 mL of DIW, and 32 μL of 10% APS aqueous solution were gently mixed in a tube. Into the tube, 3.2 μL of TEMED was added immediately before preparing the gel.

Upper gel: 1 mL of gel buffer solution, 0.16 mL of acrylamide solution, 0.84 mL of DIW, and 16 μL of 10% APS aqueous solution were gently mixed in a tube. Into the tube, 1.6 μL of TEMED was added immediately before preparing the gel.

Electrophoresis

An electrophoresis unit was kept at a low temperature by circulating ice water (1 L/hour) before running a mixture sample of electrophoresis protein and β-glucan. 2 μg of BGRP or Dectin-1-Fc, and 2 μg of BG (Laminarin, CSBG) were mixed (Sup BGRP: Laminarin, Bm BGRP: Laminarin, Dectin-1: Laminarin, Tc BGRP: CSBG), and the mixture was incubated at room temperature. The incubation was performed for 1 hour, and then a 5×sample buffer solution was added, and the obtained solution was incubated on ice for 5 minutes. The electrophoresis was performed at 100 V for the first 1 hour. After that, the output power was changed to 150 V until the electrophoresis was completed. After the electrophoresis, the gel was fixed and bleached for 1 hour in an aqueous solution containing 10% methanol and 15% acetic acid. After that, the gel was washed with DIW three times. In the end, the gel was scanned to obtain an image.

Figure 14:
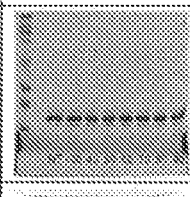
FIG. 14 is a diagram showing the results by SDS-PAGE and BN-PAGE for the changes in the β-glucan binding ability due to the heat treatment of BGRP.

<2> Results are shown in FIG. 14. All of the BGRPs did not show any change in the mobility in SDS-PAGE due to heat treatment, but Dectin-1-Fc began to aggregate at 60° C. and lost the binding activity, whereas all of the 3 kinds of BGRPs did not cause much aggregation at a high temperature and further did not lose the binding ability. Bm BGRP (B) and Tc BGRP (T) began to aggregate at 60° C. or more, but no aggregation was observed in Sup BGRP. Further, the β-glucan binding ability was not lost even after the treatment at 90° C.

---

The invention claimed is:

1. A β-glucan-binding protein having a binding ability to β-glucan, comprising: the amino acid sequence of SEQ ID NO: 1.

2. The β-glucan-binding protein according to claim 1, wherein the β-glucan is β-1,3 glucan or β-1,3-1,6 glucan.

3. The β-glucan-binding protein according to claim 1, wherein the β-glucan has a triple helical structure.

4. A β-glucan detection kit, comprising: the β-glucan-binding protein according to claim 1.

5. An artificial DNA encoding the β-glucan-binding protein according to claim 1.

6. The artificial DNA according to claim 5, comprising: the nucleotide sequence of SEQ ID NO: 2.

7. A bacterium into which the artificial DNA according to claim 5 is introduced.

8. A β-glucan detection kit, comprising: the β-glucan-binding protein according to claim 2.

9. A β-glucan detection kit, comprising: the β-glucan-binding protein according to claim 3.

10. A bacterium into which the artificial DNA according to claim 6 is introduced.

* * * * *

SEQUENCE LISTING

```
<160> NUMBER OF SEQ ID NOS: 2

<210> SEQ ID NO 1
<211> LENGTH: 149
<212> TYPE: PRT
<213> ORGANISM: Artificial Sequence
<220> FEATURE:
<223> OTHER INFORMATION: Beta-glucan-binding protein

<400> SEQUENCE: 1

Met Asn His Lys Val His His His His His Ile Glu Gly Arg His
1               5                   10                  15

Met Glu Leu Gly Thr Tyr Glu Val Pro Asp Ala Lys Leu Glu Ala Ile
            20                  25                  30

Tyr Pro Lys Gly Leu Arg Val Ser Ile Pro Asp Asp Gly Phe Ser Leu
        35                  40                  45

Phe Ala Phe His Gly Lys Leu Asn Glu Glu Met Glu Gly Leu Glu Ala
    50                  55                  60

Gly Thr Trp Ser Arg Asp Ile Thr Lys Ala Lys Asn Gly Arg Trp Thr
65                  70                  75                  80

Phe Arg Asp Arg Asn Ala Glu Leu Lys Ile Gly Asp Lys Ile Tyr Phe
                85                  90                  95
```

```
Trp Thr Tyr Val Ile Lys Asp Gly Leu Gly Tyr Arg Gln Asp Asn Gly
            100                 105                 110

Glu Trp Thr Val Thr Gly Tyr Val Asp Glu Asp Gly Asn Pro Val Asp
        115                 120                 125

Thr Asp Gly Pro Thr Thr Thr Pro Thr Gly Ser Glu Phe Lys Leu Val
    130                 135                 140

Asp Leu Gln Ser Arg
145

<210> SEQ ID NO 2
<211> LENGTH: 450
<212> TYPE: DNA
<213> ORGANISM: Artificial Sequence
<220> FEATURE:
<223> OTHER INFORMATION: Beta-glucan-binding protein

<400> SEQUENCE: 2
atgaatcaca aagtgcatca tcatcatcat catatcgaag gtaggcatat ggagctcggt      60
acctatgaag tgcctgatgc gaaactcgaa gccatttacc ccaaagggtt acgcgttagc     120
attccggatg atggcttttc gctgtttgcc ttccatggga aactgaacga ggagatggaa     180
ggtctggaag ctggaacttg gagtcgggac atcacgaaag cgaagaacgg tcgttggacc     240
tttcgtgacc gcaatgcaga gctgaaaatt ggcgacaaga tctacttctg gacctacgtc     300
atcaaagatg gcttgggtta tcgccaggat aacggagaat ggaccgtaac gggctatgtg     360
gacgaagatg gcaatccggt tgataccgat ggtccgacta cgacaccaac cggatccgaa     420
ttcaagcttg tcgacctgca gtctagatag                                     450
```